US006218543B1

(12) United States Patent
Grendze et al.

(10) Patent No.: US 6,218,543 B1
(45) Date of Patent: Apr. 17, 2001

(54) PROCESSES FOR PRODUCING HIGHLY PURE NICOTINAMIDE

(76) Inventors: Martin Grendze, 9017 Black Hawk La., Indianapolis, ID (US) 46234; Susan L. Vorhies, 2437 W. Co Rd. 350 S., Indianapolis, ID (US) 46122

(*) Notice: Subject to any disclaimer, the term of this patent is extended or adjusted under 35 U.S.C. 154(b) by 0 days.

(21) Appl. No.: 09/358,201

(22) Filed: Jul. 21, 1999

Related U.S. Application Data
(60) Provisional application No. 60/093,553, filed on Jul. 21, 1998.

(51) Int. Cl.$^7$ .................................................. C07D 213/56
(52) U.S. Cl. ................................. 546/317; 546/286
(58) Field of Search ...................... 546/317, 286

(56) References Cited

U.S. PATENT DOCUMENTS

| | | | |
|---|---|---|---|
| 3,143,465 | 8/1964 | Keating et al. | 167/65 |
| 4,314,064 | 2/1982 | Beschke et al. | 546/317 |
| 4,447,614 | 5/1984 | Beschke et al. | 546/316 |
| 4,447,615 | 5/1984 | Beschke et al. | 546/317 |
| 4,522,726 | 6/1985 | Berry et al. | 210/660 |
| 4,764,276 | 8/1988 | Berry et al. | 210/264 |
| 4,808,317 | 2/1989 | Berry et al. | 210/660 |
| 5,395,758 | 3/1995 | Takashima et al. | 435/122 |
| 5,756,750 | 5/1998 | Cao et al. | 546/319 |

FOREIGN PATENT DOCUMENTS

| | | |
|---|---|---|
| 1335502 | 7/1963 | (FR) . |
| 879551 | 10/1958 | (GB) . |
| 72 18875 | 9/1972 | (JP) . |
| 72 31983 | 11/1972 | (JP) . |
| 93007000 | 1/1993 | (JP) . |
| 77 06612 | 12/1978 | (NL) . |
| 1288183 A1 | 2/1987 | (SU) . |
| 1553530 A1 | 3/1990 | (SU) . |
| 1553531 A1 | 3/1990 | (SU) . |

OTHER PUBLICATIONS

Advanced Separation Technologies™, "The ISEP® Principle Of Continuous Adsorption", 1990.

C.F. Krewson, J.F. Couch, "The Hydrolysis Of Nicotinonitrile By Ammonia", *Notes*, vol. 65, pp. 2256–2257 (Nov. 1943).

B.V. Suvorov, A.D. Kagarlitskii, N.V. Suslova, Yu.G. Efremov, M.K. Erzhanov, "Continuous Method For Hydrolysis Of 3–Cyanopyridine To Nicotinamide And Nicotinic Acid", *J. Applied Chem. USSR*, vol. 45, pp. 2716–2718 (1972).

*Primary Examiner*—Zinna Northington Davis
(74) *Attorney, Agent, or Firm*—Woodard, Emhardt, Naughton Moriarty & McNett

(57) ABSTRACT

Described are processes for the large, commercial scale production of USP grade nicotinamide, wherein the USP grade product is isolated using novel strategies which minimize product waste, and avoid the need for crystallizations and/or ameliorate complications arising in crystallization strategies. Preferred processes involve the processing of nicotinamide reaction crudes over both cation exchange and weak base resins and the subsequent recovery of USP grade nicotinamide by simple evaporation.

27 Claims, 1 Drawing Sheet

PROCESSES FOR PRODUCING HIGHLY PURE NICOTINAMIDE

REFERENCE TO RELATED APPLICATION

This application claims priority upon U.S. patent application Ser. No. 60/093,553 filed Jul. 21, 1998, which is hereby incorporated herein by reference in its entirety.

BACKGROUND

The present invention relates generally to the preparation of nicotinamide. More particularly, the present invention relates to processes for the effective, economic, large-scale production of USP grade nicotinamide from crude nicotinamide employing both cation exchange and weak base resin treatment.

As further background, nicotinamide (also known as niacinamide and 3-pyridine carboxamide) and nicotinic acid (also known as niacin and 3-pyridine carboxylic acid), both commonly referred to as vitamin $B_3$, are members of the B-vitamin complex and precursors of coenzymes I and II. As such, these compounds are important supplements to the diet of humans and animals. Pellegra related deaths in the United States caused by vitamin $B_3$ deficiency dropped from 7,358 in 1929, to 70 in 1956, primarily as a result of increased availability of vitamin $B_3$. Higher growth rates occur in animals having diets supplemented with vitamin $B_3$ and in the case of ruminants, higher milk production also occurs.

In 1985, the U.S. market for niacinamide and niacin was estimated at 6,700 metric tons. See Kirk-Othmer, *Encyclopedia of Chemical Technology*, Third Edition, Vol. 24, pages 59–93 for a general discussion of the $B_3$ Vitamins.

These compounds have been prepared by hydrolysis of 3-cyanopyridine in batch and continuous processes with catalytic to stoichiometric excesses of a base. A majority of the methods reported have been batch processes. For example, the hydrolysis of 3-cyanopyridine with excess ammonia at 107°–109° C. for 12 hours was reported to give mixtures of nicotinamide and niacin. See J. Am Chem. Soc. 65, at pages 2256–7 (1943). In still another variation, the hydrolysis of 3-cyanopyridine has been reported with a polymeric base, Dowex 1X4 (in the hydroxide form), to yield nicotinamide. See Dutch Patent Application No. 7706612-A; CA:90:186814e. U.S. Pat. No. 4,314,064 describes the continuous hydrolysis of 3-cyanopyridine with 0.3 to 3.0 moles of an alkali metal hydroxide for each 100 moles of cyanopyridine at pressures of between 3 to 20 bars and with heating or cooling to maintain the prescribed reaction temperature. Similarly, 3-cyanopyridine is reported to react in a continuous process with aqueous ammonia at a molar ratio of 1:0.5 and a contact time of 40–50 minutes at 200°–260° C. to give nicotinamide. See Journal of Applied Chemistry of the USSR (English Translation: 45:2716–2718 (1972).

As an alternative to the hydration of cyanopyridines in the presence of bases, bacterial and enzymatic hydrolysis processes have been studied. U.S. Pat. No. 5,395,758, assigned to Sumitomo Chemical Company Ltd., describes the conversion of 3-cyanopyridine to nicotinamide using cultured broths of an Agrobacterium bacteria. Japanese Patent No. 9300770000, assigned to Nitto Chemical Ind. Co. Ltd., describes the hydration of 3-cyanopyridine using the action of Corynebacterium or Nocardia bacteria to selectively yield nicotinamide.

Because nicotinamide is commercially produced in very large scale, the recovery of the nicotinamide product, once formed, is a critical component of the overall process. This is especially true in the production of USP grade nicotinamide for human consumption, where the product must be recovered in highly pure form while nonetheless minimizing cost and technical difficulty in the workup. To date, commercial scale production of nicotinamide has involved its crystallization from crude nicotinamide product mediums. While crystallization has been demonstrated as a classic method for effectively recovering USP grade nicotinamide on a large scale, it does have drawbacks. First, crystallizations are generally time consuming, involve the use of large crystallization vessels, and necessitate a filtration step. In addition, the filtrate from the filtration step often contains significant amounts of unrecovered nicotinamide. This product either has to go to waste, or the filtrate must be recycled to subsequent crystallizations to generate additional isolated product. Such recycle process, when repeated several times, lead to a buildup of impurities in the filtrate, which makes subsequent recycles more and more difficult and eventually impracticable. Thus, a highly impure spent filtrate is eventually generated containing substantial nicotinamide, which must be stored or disposed as waste. These drawbacks are amplified when one considers the scale at which nicotinamide is produced. Nonetheless, alternative, commercially-practicable recovery strategies for USP grade nicotinamide remain to be discovered.

There are a few reports in the literature of attempts to treat certain crude nicotinamide mediums in other ways to recover nicotinamide. For example, British Patent Application 879,551 describes separating nicotinamide from a solution also containing ammonium nicotinate by passage over a column containing Amberlite IRA-400 resin, water wash, and elution with 2% nitric acid. French Patent No. 1335502 describes preparing a tasteless nicotinamide product by dissolving nicotinamide in water, mixing this medium with a non-toxic cation exchange resin to adsorb the nicotinamide onto the resin, and then washing and drying the resin. U.S. Pat. No. 3,143,465 describes the preparation of a similar style product by adsorbing nicotinamide and potentially other products onto polystyrene resins containing P(O)OH groups.

Japanese Kokai 72 18875 describes the purification of nicotinamide containing sodium or potassium nicotinate by passage through a strongly basic ion exchange resin such as Amberlite IRA 410 or IRC 50. Japanese Kokai 72 31983 describes heating 3-cyanopyridine with sodium or potassium hydroxide and water to prepare nicotinamide, diluting the resulting mixture with water to bring the nicotinamide concentration to less than 25%, and then passing the solution over a column of a strongly basic ion exchange resin. Ratajczak et al., *Przem. Chem.* 1981, 60(6), 335–7, report the use of a sulfonic acid cation exchanger, Wofatit KS-10, for the purification of the mother liquors resulting from the crystallization of nicotinamide. U.S. Pat. Nos. 4,447,614 and 4,447,615 describe a nicotinamide recovery process which involves adjusting the pH of a crude nicotinamide reaction mixture by adding acid or alkali and crystallizing the nicotinamide from 2-methylpropanol-1. The mother liquor from this crystallization is recycled and is treated from time to time either by distillation or by a sulfonated styrene-divinylbenzene copolymer and/or a strongly basic styrene-divinylbenzene copolymer quaternary ammonium resin. Atsuaki et al., *Kogyo Kagaku Zasshi* 60, 875–9 (1957), describe the treatment of a crude 30% nicotinamide solution with activated carbon for three hours, dilution with water to a final concentration of 10%, and passage through a double-bed column containing Amberlite IRA-410 and Amberlite IRC-50 at a rate of 1.8 cc/min. at 15° C.

In light of the above background there remain needs in the field of commercial nicotinamide production for efficient and economic processes for recovering highly pure forms of nicotinamide such as USP grade nicotinamide. The resent invention addresses these needs.

SUMMARY OF THE INVENTION

A feature of the present invention is the discovery of improved processes for producing nicotinamide which avoid relatively expensive recovery steps practiced in prior processes, and/or which enable maximal recovery of the produced nicotinamide and also of other useful substances such as nicotinic acid produced as byproducts. Accordingly, one preferred embodiment of the present invention provides a commercial process for producing nicotinamide which includes first reacting 3-cyanopyridine in an aqueous basic medium at a 3-cyanopyridine concentration of about 20 to about 85 weight percent to form a reacted medium containing about 20 to about 85 weight percent nicotinamide and a nicotinic acid salt. The reacted medium is treated with a cation exchange resin to remove cations and thereby convert the nicotinic acid salt to nicotinic acid, resulting in a cation-depleted aqueous medium containing about 20 to about 85 weight percent nicotinamide and nicotinic acid. The cation-depleted medium is treated with a weak base resin to remove nicotinic acid, resulting in a nicotinic acid-depleted aqueous medium containing about 20 to about 85 weight percent nicotinamide. USP grade nicotinamide is then recovered by evaporation. In this manner, USP grade nicotinamide is produced without the need for crystallization and filtration, the latter steps representing a relatively expensive and time-consuming process.

Another preferred embodiment of the present invention provides a process for recovering a USP grade nicotinamide product from an aqueous medium containing nicotinamide and sodium nicotinate. In this inventive process, cations are removed from the medium to convert sodium nicotinate to nicotinic acid. The nicotinic acid is removed from the medium, and then water is evaporated, so as to yield USP grade nicotinamide.

A further preferred embodiment of the present invention relates to a commercial process for producing USP grade nicotinamide, which involves a crystallization and filtration step, recycle of the resulting filtrate to recover nicotinamide therein, all coupled with ion exchange processing to mitigate the buildup of nicotinic acid salts in the recycled filtrate. The process includes the steps of:

(a) reacting 3-cyanopyridine in an aqueous base at a 3-cyanopyridine concentration of about 20 to about 85 weight percent to form a reacted medium containing about 20 to about 85 weight percent nicotinamide, and a nicotinic acid salt;

(b) treating the reacted medium with a cation exchange resin to remove cations and thereby convert the nicotinic acid salt to nicotinic acid, resulting in a cation-depleted aqueous medium containing about 20 to about 85 weight percent nicotinamide, and nicotinic acid;

(c) treating the cation-depleted medium with a weak base resin to remove nicotinic acid, resulting in a nicotinic acid-depleted aqueous medium containing about 20 to about 85 weight percent nicotinamide;

(d) concentrating the nicotinic acid-depleted medium by evaporating water under heated conditions;

(e) cooling the nicotinic acid-depleted medium after step (d) so as to crystallize nicotinamide;

(f) filtering the product of step e) to recover crystalline nicotinamide and form a filtrate containing unrecovered nicotinamide;

(g) repeating steps (a)–(c);

(h) combining the filtrate from step (f) with the nicotinic acid-depleted aqueous medium obtained in step (g);

(i) concentrating the product of step (h) by evaporating water under heated conditions;

(j) cooling the product of step (i) so as to crystallize nicotinamide; and (k) filtering the product of step (j) to recover crystalline nicotinamide.

A still further preferred embodiment of the invention provides a process for producing nicotinamide and nicotinic acid. This process includes first reacting 3-cyanopyridine with an aqueous base to form a reacted medium containing nicotinamide and a nicotinic acid salt. The reacted medium is treated with a cation exchange resin to bind cations to the resin and thereby convert the nicotinic acid salt to nicotinic acid, resulting in a cation-depleted aqueous medium containing nicotinamide, and nicotinic acid. An acidic eluent is then passed over the cation exchange resin to result in an acidic effluent. The cation-depleted medium is treated with a weak base resin to bind nicotinic acid to the resin, resulting in a nicotinic acid-depleted aqueous medium containing nicotinamide. A basic eluent is passed over the weak base resin to result in a basic effluent containing a nicotinic acid salt. The acidic effluent is combined with the basic effluent to convert the nicotinic acid salt to nicotinic acid. In this fashion, the production and recovery of the major product, nicotinamide, is efficiently coupled to the production and recovery of nicotinic acid. At the same time, the acidity of the acidic effluent, and the basicity of the basic effluent, are effectively neutralized, as would be required in any event for disposal.

In its several embodiments, the present invention provides improved processes for producing USP grade nicotinamide with reduced recovery costs and/or more effective recovery of nicotinamide and useful co-products such as nicotinic acid. The preferred processes employ efficient, economic techniques utilizing cation-exchange and weak base resins, which can either completely eliminate the need for crystallization/filtration to yield USP grade nicotinamide, facilitate repeated recycling of filtrate from the filtration step, or take the filtrate nicotinamide to USP grade material without the need for subsequent crystallization. These and other features and advantages of the invention will be readily apparent to the skilled artisan upon reviewing the descriptions herein.

DESCRIPTION OF THE PREFERRED EMBODIMENTS

Figure 1:
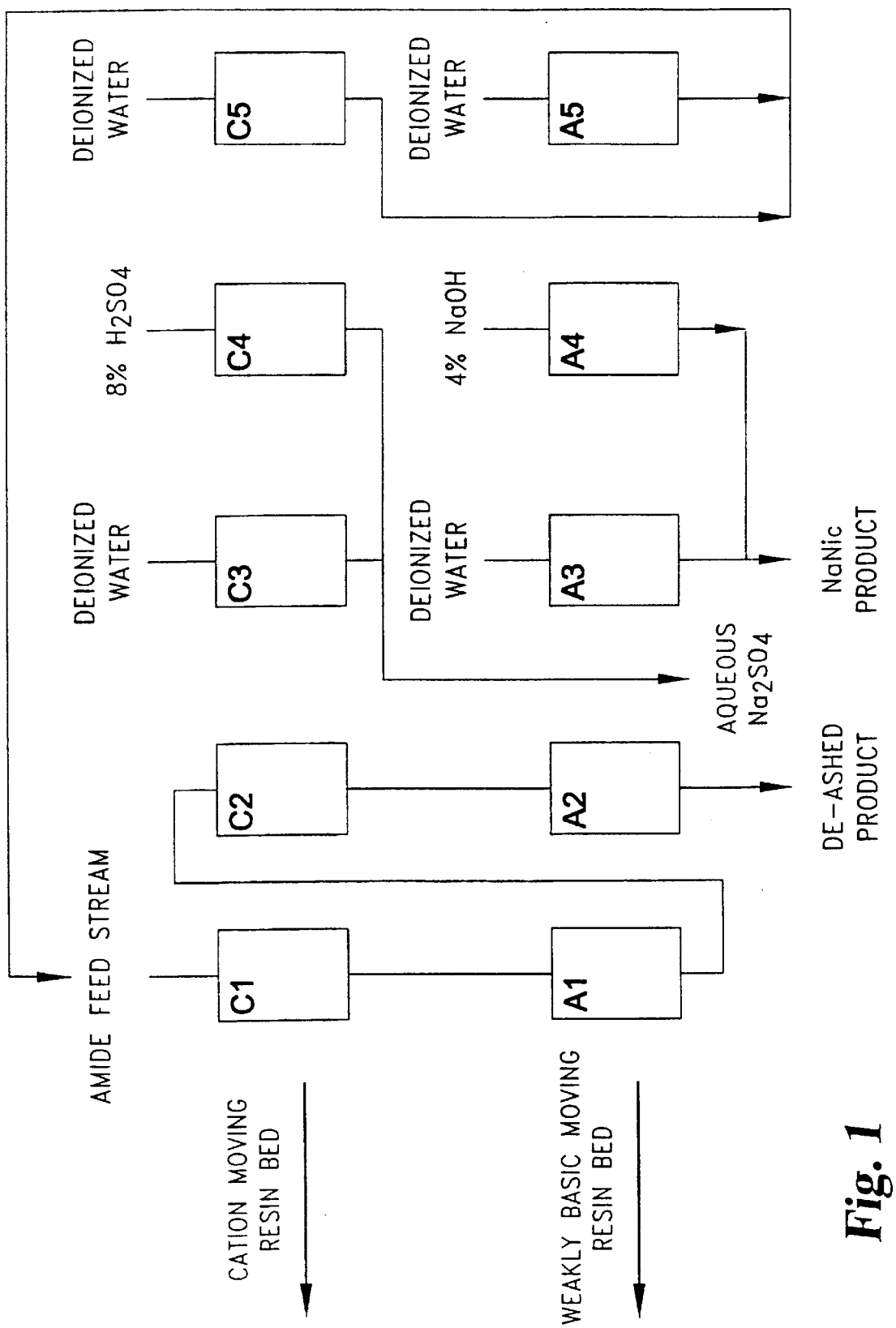
FIG. 1 provides a schematic diagram of a preferred USP nicotinamide production process of the invention employing a dual continuous contacting apparatus setup to treat an impurity-containing nicotinamide product medium with cation-exchange and weak base resins.

For the purposes of promoting an understanding of the principles of the invention, reference will now be made to certain of its embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As disclosed above, features of the present invention involve improved processes for producing "USP grade"

nicotinamide, which refers to a nicotinamide product which meets the drug product standards published in the United States Pharmacopeia Volume XXIII (1995). In this regard, said United States Pharmacopeia provides following standards for a USP grade nicotinamide product:

| Assay | Requirement |
|---|---|
| Identification A-IR | Pass |
| Identification B-UV (FCC) | Pass (0.63–0.67) |
| Assay by UV (JP) | 98.5 minimum |
| Melting Range (FCC) | 128–131° C. |
| Loss on Drying (FCC) | 0.5% maximum final |
| Residue on Ignition (FCC) | 0.1% maximum |
| Heavy Metals (FCC) | 0.002% maximum |
| Nicotinamide by HPLC | 98.5–101.5% |

In accordance with one aspect of the invention, a USP grade nicotinamide product can be obtained absent any crystallization following production of the nicotinamide in crude form. In particular, the crude nicotinamide can be formed by reacting 3-cyanopyridine, at least one base, and water to provide a reacted medium containing nicotinamide. The reacted medium will typically also contain impurities including nicotinic acid salt and/or nicotinic acid and/or 3-cyanopyridine. The hydrolysis reaction to form the nicotinamide can be conducted in any suitable fashion, including for example batch or continuous modes. Suitable hydrolysis processes are described, for example, in U.S. Pat. Nos. 5,756,750 and 4,314,064.

In such processes, at least one mole of water will generally be used per mole of 3-cyanopyridine, and more typically at least a slight molar excess of water will be used relative to 3-cyanopyridine. This can be conveniently achieved by charging 3-cyanopyridine to an aqueous medium to a level of about 20% to about 85% by weight 3-cyanopyridine. In preferred process forms, the 3-cyanopyridine is charged to a level of about 30% to about 60% of the reaction medium. As to the base, its choice and the level of its use are parameters that are well within the purview of those of ordinary skill in the art. The base may be soluble or insoluble in the reaction medium. For example, ammonia or water-soluble alkali metal hydroxides or alkaline earth metal hydroxides are often used, especially sodium hydroxide and potassium hydroxide. Heterogeneous base catalysts may also be used. For example, a particulate, basic resin, such as a resin containing basic amino groups, may be slurried into the reaction medium to catalyze the hydrolysis of 3-cyanopyridine to nicotinamide. With stronger bases such as sodium and potassium hydroxide, smaller quantities of base are adequate, while with weaker bases such as ammonia, larger quantities of base are required. Control of these parameters to achieve the desired products or product mixtures will be well within the purview of one skilled in the art given the teachings herein.

Generally, about 0.01 to about 50 equivalents of base will be used per 100 moles of 3-cyanopyridine. In this regard, the number of equivalents of base will be determined in the usual fashion, taking into account whether the base is monobasic, dibasic, etc. Thus, the number of equivalents of base will be determined by multiplying the number of moles of a base by the number of protons that a mole of that base will react with. In preferred forms of the invention wherein an alkali metal hydroxide is employed as the base, about 0.3 to 5 moles of alkali metal hydroxide will be used per 100 moles of 3-cyanopyridine, more preferably about 0.5 to 3.0 moles of alkali metal hydroxide per 100 moles of 3-cyanopyridine.

In one convenient form, the hydrolysis process can be carried out in a 1% to 20% aqueous alkali metal hydroxide solution, more typically about 1% to about 10%. The alkali metal hydroxide can be added all at the beginning of the reaction, or in portions over the course of the reaction. Such reactions yield a crude nicotinamide product containing an alkali metal nicotinate (e.g. sodium or potassium nicotinate), nicotinic acid, and 3-cyanopyridine.

The temperature and duration of the reaction may vary so long as the conditions utilized are sufficient to drive the hydrolysis of 3-cyanopyridine to substantial completion, e.g. achieving a conversion greater than about 80%, more preferably greater than about 95%. The reaction temperature will usually be in the range of about 100° C. to about 250° C., more typically about 120° C. to about 200° C. The reaction can be run continuously under controlled temperature and pressure conditions, for example as described in U.S. Pat. No. 4,314,064, or under adiabatic temperature conditions as described for instance in U.S. Pat. No. 5,756,750. The duration of the reaction will vary with the temperature, the strength of the base catalyst and other similar factors, but typically will be in the range of about 1 to about 30 minutes and preferably in the range of about 1 to 15 minutes for continuous processes, and about 1 to about 60 minutes for large batch processes.

For the preferred continuous processes, high production rates, selectivities, and yields are typically obtained. For instance, for nicotinamide formation by hydrolysis of 3-cyanopyridine, production rates ranging from between about 200 to several thousand kg per hour per liter of reactor volume can be obtained, more about 200 to about 1000 kg per hour per liter and most often about 400 to about 900 kg per hour per liter. Given the scale of commercial processes, this results in the production of at least about 150 kg of nicotinamide per hour, typically in the range of about 150 kg to about 1000 kg, in a crude reaction medium that totals at least about 100 liters per hour, typically in the range of about 100 to about 1000 liters per hour. The yields of nicotinamide in preferred continuous processes have typically ranged between about 95% to about 99.5%.

The above-described hydrolysis processes generally result in reacted mediums containing nicotinamide and impurities, the impurities including nicotinate salts, nicotinic acid, and 3-cyanopyridine. The nicotinate salts are usually present in a range of about 0.05% to about 5.0% by weight of the reacted medium, the nicotinic acid about 0.1% to about 5% by weight, and the 3-cyanopyridine about 0.05% to about 0.5% by weight. Such crude reaction mediums, in past commercial processes, have been subjected to concentration, pH adjustment with base, crystallization and filtration to isolate USP grade nicotinamide products.

One feature of the present invention is the discovery that USP grade nicotinamide can be commercially produced absent crystallization of the nicotinamide, if the reaction crude is processed and the nicotinamide isolated as described herein. In particular, an inventive process involves treatment of the reaction crude with both a cation exchange resin and a weak base resin. Treatment with a cation exchange resin effectively removes counter cations of nicotinate salts, e.g. sodium, potassium or ammonium ions, while treatment with the weak base resin effectively removes nicotinate ions.

The cation exchange resin may be selected from those available both commercially and through known preparative techniques. Preferred cation exchange resins have functional groups selected from sulfonic acid or other strongly acidic functionalities incorporated in a crosslinked copolymer structure. The crosslinked polymer structure is desirably a copolymer of styrene and divinylbenzene. Illustrative commercially-available cation exchange resins include, for instance, Dowex Marathon C, Dowex 50WX2, Dowex 50WX4, Dowex 50WX8, Amberlite IR-122, and Amberlite 200.

The weak base resin can likewise be selected from among those available commercially or through known preparative techniques. The preferred weak base resins will include amino groups incorporated in a crosslinked polymer structure, in base form. In this regard, it has been found that strong base resins, particularly those incorporating quaternary ammonium functions, tend to deleteriously catalyze hydrolysis of the nicotinamide product to nicotinic acid. Thus, in the present invention, a weaker base resin will be employed which avoids the occurrence of such hydrolysis to any significant extent. The amino groups of these weak base resins are preferably aliphatic amino groups, for example including for instance monoalkylamino or dialkylamino groups, especially wherein the alkyl groups contain from 1 to about 5 carbon atoms. Thus, illustrative amino groups will include dimethylamino, methylethylamino, diethylamino, dipropylamino, dibutylamino, etc. The crosslinked polymer structure of the resin is advantageously a copolymer of styrene and divinylbenzene. Suitable commercially available weak base resins which can be used in the invention include Amberlyst A21, Dowex Marathon C, Dowex WGR-2, Amberlite IRA-93, and Amberlite IRA-68.

The treatment over the resins is desirably conducted in a continuous fashion, in a contacting unit equipped to treat the solutions at a rate of at least about 0.1 gallon per minute per foot squared, typically falling generally in the range of about to about 1 gallon per minute per foot squared to about 10 gallons per minute per foot squared. Linear flow rates of about 1 gallon per minute per foot squared to about 4 gallons per minute per foot squared are preferred.

Favored USP nicotinamide isolation processes of the invention are conducted using one or more preparative-scale contacting apparatuses including a plurality of resin columns and means for passing the streams to be treated and eluent streams through the columns. A more preferred such apparatus is a continuous contacting apparatus ("CCA") For example, continuous contacting apparatuses which are useful in the invention include those such as the ISEP or CSEP Continuous Contactors available from Advanced Separations Technology, Inc. (AST, Inc.), Lakeland, Fla., and are also generally described in U.S. Pat. No. 4,764,276 issued Aug. 16, 1988, U.S. Pat. No. 4,808,317 issued Feb. 28, 1989 and U.S. Pat. No. 4,522,726 issued Jun. 11, 1985. A brief description of such a CCA device as described in these patents is set forth below. For further details as to the design and operation of CCA's suitable for use in the invention, reference can be made to literature available from AST, Inc. including "The ISEP™ Principle Of Continuous Adsorption", and as well to the above-cited U.S. patents.

The preferred CCA for use in the present invention will be a liquid-solid contacting apparatus including a plurality of chambers which are adapted to receive ion exchange resin and which taken together or separately may provide a contacting zone for processes of the invention. The chambers have respective inlet and outlet ports, and are mounted for rotation about a central axis so as to advance the chambers past supply and discharge ports which cooperate with the inlet and outlet ports. In particular, liquid is supplied individually to inlet ports at the top of these chambers through conduits connected with a valve assembly above the chambers, which valve assembly provides a plurality of supply ports which cooperate with inlet ports of the chambers as they are advanced. Similarly, conduits connect the outlet port at the lower end of each chamber with a valve assembly below the chambers which provides discharge ports which cooperate with the outlet ports as the chambers are advanced. The valve assemblies include movable plates with slots that cover and uncover inlet ports as the plate rotates with the carousel. By varying the size of the slots in the plate and the location of the slots, the flow from the supply conduits into the chamber and flow from the chamber to the exhaust conduits can be controlled in a predetermined manner. The motion of one plate over the other can be continuous or as an indexed motion. The time during which liquid flows into and out of the chambers is a function of the speed of rotation of the chambers about the central axis.

Two such CCA apparatuses are preferably used in processing in accordance with the invention. A first such apparatus is loaded with the cation exchange resin, and a second with the weak base resin, and the reaction crude is fed from one to the other for successive processing over the resins. The feed stream is preferably divided for simultaneous feed through a plurality of resin columns, for example five columns, and then recombined for feed to the adjoining contacting unit. In this fashion, large, commercial scale volumes of reaction crude can be relatively rapidly processed, while nonetheless achieving effective removal of sodium and nicotinate ions.

In a most preferred embodiment, the reaction crude is passed successively over a cation exchange, a weak base, a cation exchange and then a weak base resin, followed by evaporation, to produce a USP grade niacinamide product. Using two contacting units, as illustrated in FIG. 1, this can be achieved by passing the reacted medium and intermediately-treated mediums back and forth among the two continuous contacting apparatuses. FIG. 1 is a schematic diagram representing the plumbing and flow pattern of a dual-CCA setup. In FIG. 1, the upper block row including C1 through C5 represents a first CCA loaded with cation exchange resin, and the lower block row including A1 through A5 represents a second CCA loaded with weak base resin. The crude amide feed stream is passed downflow through resin bed C1, which could represent a single resin column or container but preferably represents a plurality of containers of resin. After exiting C1, the first-cation-treated stream, depleted of cations, is passed to resin bed A1 of the second CCA. Resin bed A1 also could be a single resin container but is preferably multiple containers through which the stream is passed upflow or downflow, desirably upflow. The first-base-treated medium exiting A1, now depleted of nicotinate ions, is conveyed back to the first CCA unit, where it is passed again through a similar resin bed C2 composed of one or multiple resin-filled containers. Exiting C2, the second-cation-treated stream, now further depleted of cations, is conveyed to the second CCA. There, the stream is passed through resin bed A2, comprised of one ore multiple resin-filled containers. The resin bed A2 completes the resin purification of the product, which can then simply be evaporated to recover a USP grade nicotinamide. In this illustrated system, the streams can be conveyed downflow or upflow through the beds. Downflow processing is preferred for the cation exchange resin in this setup, whereas upflow is preferred for the weak base resin.

As shown, after successively treating the first-base-treated stream and then the reaction crude in their travel path, the cation exchange resin beds are washed with deionized water, e.g. at C5, stripped with a strong acid solution such as sulfuric acid, e.g. at C4, and then washed again with deionized water. The stream resulting from the first wash will contain some residual nicotinamide and is combined with the amide feed stream to the system. The stream resulting from the acid strip, containing the salt of the cation and acid, for example sodium sulfate, is combined with the stream from the second water wash to form an acid salt stream.

In the second CCA unit, after successively processing the second-cation-treated stream and then first-cation-treated stream, the weak base resin is washed with deionized water, e.g. at A5. The exit stream from the first water wash is fed to and combined with the crude nicotinamide feed stream. After the first wash, the weak base resin bed is stripped with a basic solution, for example sodium hydroxide, to remove the nicotinate ions. The exit stream from this strip will thus contain a nicotinate salt such as sodium nicotinate. This exit stream is combined with the exit stream from a subsequent wash with deionized water, e.g. at A3, to form a nicotinate salt (e.g. sodium nicotinate) stream.

In another aspect of the present invention, the basic nicotinate salt stream can be combined with the acidic acid salt stream to convert the sodium nicotinate to nicotinic acid. An additional amount of strong acid may be added, if necessary, to facilitate precipitation of nicotinic acid from this combined medium. In this fashion, the economics of the overall process are improved, as it produces both nicotinamide and nicotinic acid, the latter also representing a valuable food additive.

During processing over the resin, the crude nicotinamide and intermediately-processed streams are maintained at a temperature that prevents precipitation of the nicotinamide and any nicotinic acid in the medium. Typically the stream temperature will be maintained at a temperature above about 35° C. and usually in the range of about 35° C. to 100° C., more preferably in the range of about 40° C. to about 80° C.

Processing as described above can be used not only to efficiently and economically isolate USP grade nicotinamide directly from a crude nicotinamide reaction medium, but also other crude nicotinamide mediums. For example, in some processes nicotinamide is recovered from a crude reaction medium by processes including cooling to cause crystallization of the nicotinamide, and subsequent filtration. The filtrate from this step often contains significant amounts of unrecovered nicotinamide (for example about 20% to about 80% by weight), along with sodium nicotinate (about 0.1% to 5% by weight), nicotinic acid (about 1% to 15% by weight), and 3-cyanopyridine (about 0.05% to 1% by weight). Such filtrate mediums can also be treated in accordance with the invention to isolate a highly purified (e.g. USP) nicotinamide product without the need for further crystallization steps.

In a still further aspect of the invention, resin purification is used in combination with crystallization/filtration to recover USP nicotinamide. In this process, the resin purification is applied as described above prior to the crystallization, to effectively minimize buildup of impurities, especially nicotinate salts and nicotinic acid, in the filtrate as it is repeatedly recycled to isolate more unrecovered nicotinamide. The buildup of nicotinic acid can be particularly problematic. It is less soluble in water than nicotinamide, and thus tends to crystallize first from aqueous solution. This in turn seeds the crystallization of the nicotinamide in a fashion that dramatically reduces the size of the nicotinamide crystals. The small nicotiniamide crystals are less advantageously handled and utilized than larger ones, and thus avoidance of their occurrence is desirable. In addition, the use of the above-described resin purification with a nicotinamide reaction crude prior to the crystallization step can eliminate or at least reduce the need to adjust the pH of the crude with base, thus eliminating or minimizing this complicating and costly step from the manufacturing process. More preferred processes thus occur where the resin purification is applied, and no pH-adjusting base is added, prior to a crystallization/filtration step to yield USP grade nicotinamide.

Nicotinamide products produced in accordance with the present invention, isolated either by crystallization or by evaporation, may be conventionally used as food additives. The preferred processes are conducted so as to achieve nicotinamide of high purity, e.g. 99.5% or greater, and most preferably so as to yield USP grade nicotinamide.

For the purposes of promoting a further understanding of the present invention and its preferred features and embodiments, the following examples are being provided. It will be understood, however, that these examples are illustrative, and not limiting, in nature.

EXAMPLE 1

In this Example a USP grade nicotinamide product was recovered from a crude nicotinamide product medium. The crude contained 39.7% nicotinamide, 2.15% sodium nicotinate and 0.14% 3-cyanopyridine. These and all other percentages given in this Example are percentages by weight unless indicated otherwise. The total sodium content of the medium was 0.38%. On a dry basis, the reaction crude contained 93.7% nicotinamide, 5.07% sodium nicotinate, 0.33% 3-cyanopyridine, and 0.9% total sodium. Cation and weak base resins were utilized in the recovery process. The cation exchange resin was Dowex Marathon C, a sulfonated copolymer of styrene and divinylbenzene (gel form). The weak base resin was Dowex Marathon WBA, a dimethylamine-functionalized chloromethylated copolymer of styrene and divinylbenzene (macroporous form with a monodisperse size distribution). After washing with deionized water, these resins were loaded into columns each having an inner diameter of 15 mm and a height of 30 cm, leaving about 1.5 inches head space at the top of the columns. The reaction crude was then successively treated over the cation-exchange resin (at 28 ml/min), the weak base resin (20 ml/min), the cation-exchange resin (28 ml/min), and the weak base resin (20 ml/min). The cation-exchange resin was regenerated after every ten bed volumes of reaction crude, by a cycle that included a water wash (20 ml/min, 1.25 bed volumes), a 12% sulfuric acid strip (7 ml/min, 1 bed volume), and another water wash (20 ml/min, 1.25 bed volumes). The weak base resin was regenerated after every five bed volumes of reaction crude, by a cycle including a water wash (20 ml/min, 1.6 bed volumes), a 4% sodium hydroxide strip (20 ml/min, 1 bed volume), and another water wash (2.6 bed volumes). The feeds were analyzed by HPLC after the first pass cation-exchange and weak base, and second pass cation-exchange and weak base. Typical results from such experiments are presented in Table 1 below, top. The lower section of Table 1 gives a typical product analysis on a water free basis. The extreme right hand column of Table 1 sets out the results of an analysis of the product after recovery by evaporation (no crystallization performed). As can be seen, this processing reduced the 0.9% initial sodium to an undetectable level, and the initial 5.07% nicotinate to 0.13% (as nicotinic acid) on a dry weight basis, providing a USP grade nicotinamide.

TABLE 1

| Component | Feed | Cation Pass 1 | Base Pass 1 | Cation Pass 2 | Base Pass 2 | Dry Product |
|---|---|---|---|---|---|---|
| Amide | 39.7 | 37.4 | 30.2 | 28.8 | 20.8 | 100.8 |
| Nicotinate | 2.2 | 2.1 | 0.5 | 0.9 | 0.04 | 0.13 |
| 3-CyP | 0.14 | 0.12 | 0.1 | 0.06 | 0.06 | 0 |
| Sodium | 0.4 | 0.05 | 0.03 | 0 | 0 | 0 |
| Dry Weight | | | | | | |
| Amide | 93.7 | 94.4 | 97.1 | 96.2 | 99.5 | |
| Nicotinate | 5.1 | 5.2 | 1.7 | 3.0 | 0.2 | |
| 3-CyP | 0.3 | 0.3 | 0.2 | 0.2 | 0.3 | |
| Sodium | 0.9 | 0.1 | 0.1 | 0 | 0 | |

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. In addition, all publications cited herein are indicative of the level of skill in the art and are hereby incorporated by reference in their entirety as if each had been individually incorporated by reference and fully set forth.

What is claimed is:

1. A commercial process for producing nicotinamide, comprising:
   reacting 3-cyanopyridine with water in the presence of a base at a 3-cyanopyridine concentration of about 20 to about 85 weight percent to form a reacted medium containing about 20 to about 85 weight percent nicotinamide, and a nicotinic acid salt;
   treating the reacted medium with a cation exchange resin to remove cations and thereby convert said nicotinic acid salt to nicotinic acid, resulting in a cation-depleted aqueous medium containing about 20 to about 85 weight percent nicotinamide, and nicotinic acid;
   treating the cation-depleted medium with a weak base resin to remove nicotinic acid, resulting in a nicotinic acid-depleted aqueous medium containing about 20 to about 85 weight percent nicotinamide; and
   isolating said nicotinamide in USP grade by evaporation.

2. The process of claim 1, wherein said aqueous basic medium contains said 3-cyanopyridine in a concentration of about 30 to about 60 weight percent.

3. The process of claim 2, wherein said nicotinic acid salt is present in said reacted medium at a concentration of about 0.05 to about 5 weight percent.

4. The process of claim 3, wherein said treating steps are conducted in a continuous contacting apparatus.

5. The process of claim 3, wherein said recovering comprises passing said nicotinic acid-depleted aqueous medium over a falling film evaporator.

6. The process of claim 1, also comprising:
   providing a melt of said USP grade nicotinamide;
   causing said melt to solidify to a mass; and
   reducing said mass to a particulate nicotinamide product.

7. The process of claim 6, wherein said causing includes coating said melt onto a cooled surface to form a solidified layer of substantially pure nicotinamide, and said reducing includes flaking said solidified layer.

8. A process for preparing a USP grade nicotinamide product, comprising:
   providing an aqueous medium containing nicotinamide and sodium nicotinate;
   removing cations from the medium to convert sodium nicotinate to nicotinic acid in the medium;
   removing the nicotinic acid from the medium; and
   evaporating water from the medium to obtain a USP grade nicotinamide.

9. The process of claim 8, wherein said removing cations comprises passing said aqueous medium over a cation exchange resin to form a cation-depleted medium, and said removing nicotinic acid comprises passing the cation-depleted medium over a weak base resin.

10. The process of claim 9, wherein said passing steps are conducted in a continuous contacting apparatus.

11. The process of claim 10, wherein said weak base resin has aliphatic amino groups.

12. The process of claim 11, wherein said aqueous medium comprises a filtrate from a nicotinamide crystallization and filtration.

13. The process of claim 11, wherein said aqueous medium comprises a crude reaction medium obtained by hydrolyzing 3-cyanopyridine to nicotinamide in the presence of water and a base.

14. The process of claim 13, wherein said aqueous medium comprises about 0.05 to about 5 weight percent nicotinic acid salt.

15. A commercial process for producing nicotinamide according to claim 1, comprising:
   (a) reacting 3-cyanopyridine in an aqueous base at a 3-cyanopyridine concentration of about 20 to about 85 weight percent to form a reacted medium containing about 20 to about 85 weight percent nicotinamide, and a nicotinic acid salt;
   (b) treating the reacted medium with a cation exchange resin to remove cations and thereby convert said nicotinic acid salt to nicotinic acid, resulting in a cation-depleted aqueous medium containing about 20 to about 85 weight percent nicotinamide, and nicotinic acid;
   (c) treating the cation-depleted medium with a weak base resin to remove nicotinic acid, resulting in a nicotinic acid-depleted aqueous medium containing about 20 to about 85 weight percent nicotinamide;
   (d) concentrating the nicotinic acid-depleted medium by evaporating water under heated conditions;
   (e) cooling the nicotinic acid-depleted medium after step (d) so as to crystallize nicotinamide;
   (f) filtering the product of step e) to recover crystalline nicotinamide and form a filtrate containing unrecovered nicotinamide;
   (g) repeating steps (a)–(c);
   (h) combining the filtrate from step (f) with the nicotinic acid-depleted aqueous medium obtained in step (g);
   (i) concentrating the product of step (h) by evaporating water under heated conditions;
   (j) cooling the product of step (i) so as to crystallize nicotinamide; and
   (k) filtering the product of step (j) to recover crystalline nicotinamide.

16. The process of claim 15, wherein said steps (b) and (c) are conducted with a continuous contacting apparatus.

17. The process of claim 16, wherein said reacted medium comprises at least about 0.05 weight percent nicotinic acid salt.

18. The process of claim 17, wherein said reacted medium comprises from about 0.05 to about 5 weight percent nicotinic acid salt.

19. The process of claim 17, wherein said aqueous base is an aqueous alakline earth metal hydroxide or an aqueous alkali metal hydroxide.

20. The process of claim 19, wherein said aqueous base is aqueous sodium hydroxide.

21. A process producing nicotinamide and nicotinic acid, comprising:
  (a) reacting 3-cyanopyridine in an aqueous base at a 3-cyanopyridine to form a reacted medium containing nicotinamide and a nicotinic acid salt;
  (b) treating the reacted medium with a cation exchange resin to bind cations to the resin and thereby convert said nicotinic acid salt to nicotinic acid, resulting in a cation-depleted aqueous medium containing nicotinamide, and nicotinic acid;
  (c) passing an acidic eluent over the cation exchange resin after step (b) to result in an acidic effluent;
  (d) treating the cation-depleted medium from step (b) with a weak base resin to bind nicotinic acid to the resin, resulting in a nicotinic acid-depleted aqueous medium containing nicotinamide;
  (e) passing a basic eluent over the weak base resin after step (d) to result in a basic effluent containing a nicotinic acid salt; and
  (f) combining the acidic effluent from step (c) with the basic effluent from step (d) to convert the nicotinic acid salt to nicotinic acid.

22. The process of claim 21, wherein said acidic eluent is an aqueous strong acid.

23. The process of claim 22, wherein said acidic eluent is aqueous hydrochloric acid or aqueous sulfuric acid.

24. The process of claim 22, wherein said basic eluent is an aqueous alkali metal hydroxide or an aqueous alkaline earth metal hydroxide.

25. The process of claim 24, wherein said basic eluent is aqueous sodium hydroxide.

26. The process of claim 8, wherein:
  said aqueous medium contains 20% to 85% aqueous nicotinamide, 0.05% to 5% nicotinate salt, and 0.1% to 5% nicotinic acid;
  said removing cations comprises treating the medium at a temperature of 35° C. to 100° C. with a cation exchange resin to remove cations and result in a cation-depleted medium containing about 30% to about 60% nicotinamide; and
  said removing the nicotinic acid comprises treating the cation-depleted medium at a temperature of 35° C. to 100° C. with a weak base resin to remove nicotinate ions, resulting in a nicotinate-ion-depleted aqueous medium containing about 30% to about 60% nicotinamide.

27. A commercial process for producing nicotinamide according to claim 1, comprising:
  (a) reacting 3-cyanopyridine in an aqueous base at a 3-cyanopyridine concentration of about 20 to about 85 weight percent to form a reacted medium containing about 20 to about 85 weight percent nicotinamide, and a nicotinic acid salt;
  (b) treating the reacted medium with a cation exchange resin to remove cations and thereby convert said nicotinic acid salt to nicotinic acid, resulting in a cation-depleted aqueous medium containing about 20 to about 85 weight percent nicotinamide, and nicotinic acid;
  (c) treating the cation-depleted medium with a weak base resin to remove nicotinic acid, resulting in a nicotinic acid-depleted aqueous medium containing about 20 to about 85 weight percent nicotinamide;
  (d) concentrating the nicotinic acid-depleted medium by evaporating water under heated conditions;
  (e) cooling the nicotinic acid-depleted medium after step (d) so as to crystallize nicotinamide; and
  wherein steps (b)–(e) are conducted without the addition of any base for pH adjustment.

* * * * *